United States Patent

Sauer et al.

[11] Patent Number: 5,993,402
[45] Date of Patent: *Nov. 30, 1999

[54] PRESSURE RELIEF VALVE FOR AN ORAL IRRIGATOR

[75] Inventors: Michael Sauer, Bad Camberg; Norbert Schaefer, Frankfurt, both of Germany

[73] Assignee: Braun AG, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/958,354

[22] Filed: Oct. 27, 1997

[30] Foreign Application Priority Data

Nov. 6, 1996 [DE] Germany .................. 196 45 643

[51] Int. Cl.$^6$ ........................................ A61H 9/00
[52] U.S. Cl. ........................................ 601/162
[58] Field of Search ................ 433/80; 601/162, 601/163, 164, 165

[56] References Cited

U.S. PATENT DOCUMENTS

| | | | |
|---|---|---|---|
| Re. 27,274 | 1/1972 | Mattingly | 128/66 |
| 1,933,454 | 10/1933 | Sidney | 277/45 |
| 3,209,956 | 10/1965 | McKenzie | 222/318 |
| 3,216,619 | 11/1965 | Richards et al. | 222/74 |
| 3,227,158 | 1/1966 | Mattingly | 128/66 |
| 3,420,228 | 1/1969 | Kalbfeld | 128/66 |
| 3,501,203 | 3/1970 | Falk | 303/6 |
| 3,590,813 | 7/1971 | Roszyk | 128/66 |
| 3,896,845 | 7/1975 | Parker | 137/493.3 |
| 4,001,526 | 1/1977 | Olson | 200/16 D |
| 4,108,167 | 8/1978 | Hickman et al. | 128/66 |
| 4,109,650 | 8/1978 | Peclard | 128/66 |
| 4,201,200 | 5/1980 | Hubner | 601/162 |
| 4,302,186 | 11/1981 | Cammack et al. | 433/80 |
| 4,382,167 | 5/1983 | Maruyama et al. | 200/153 |
| 4,412,823 | 11/1983 | Sakai et al. | 433/80 |
| 4,442,831 | 4/1984 | Trenary | 128/66 |
| 4,585,415 | 4/1986 | Hommann | 433/80 |
| 4,648,369 | 3/1987 | Wannenwetsch | 123/467 |
| 4,655,198 | 4/1987 | Hommann | 128/66 |
| 4,824,368 | 4/1989 | Hickman | 433/80 |
| 4,923,602 | 5/1990 | Blood | 210/117 |
| 4,989,590 | 2/1991 | Baum et al. | 601/163 |
| 5,344,317 | 9/1994 | Paecher et al. | 433/85 |
| 5,399,089 | 3/1995 | Eichmann et al. | 433/80 |
| 5,477,829 | 12/1995 | Hassinger et al. | 123/467 |
| 5,735,582 | 4/1998 | Eith et al. | 137/596.17 |

FOREIGN PATENT DOCUMENTS

| | | |
|---|---|---|
| 085 795 B1 | 4/1987 | European Pat. Off. . |
| 14 66 963 | 5/1969 | Germany . |
| 25 45 936 | 4/1977 | Germany . |
| 29 10 982 | 10/1980 | Germany . |
| 31 31 995 A1 | 2/1983 | Germany . |
| 33 47 239 C2 | 2/1993 | Germany . |
| 56-68447 | 6/1981 | Japan . |
| 655 237 A5 | 4/1986 | Switzerland . |
| 1182031 | 2/1970 | United Kingdom . |

*Primary Examiner*—John J. Wilson
*Attorney, Agent, or Firm*—Edward S. Podszus

[57] ABSTRACT

The invention is directed to an oral irrigator for the care and cleaning of teeth and gums, which is provided with a pump (1) adapted to be driven by an electric motor. The pump (1) has an inlet (2) connected in particular to a liquid reservoir and provided with an inlet valve (8), an outlet (3) connected in particular to a jet nozzle and provided with an outlet valve (21), as well as a pump cylinder (5) connected to the inlet (2) and the outlet (3). The pump cylinder (5) has a piston (4) reciprocating therein, whereby liquid can be drawn from the inlet (2) into the pump cylinder (5) following which the drawn liquid can be delivered from the pump cylinder (5) to the outlet (3). The inlet valve (8) includes a pressure relief valve (13) through which liquid can be delivered from the pump cylinder (5) to the inlet (2) in the event of excess pressure building up. It is thus sufficient to provide on the jet nozzle only a shut-off valve (25) for shutting off the water pumped to the jet nozzle. It is not necessary for the electric on-off switch of the pump (1) to be located on the jet nozzle, but it may be disposed on the housing of the oral irrigator.

22 Claims, 1 Drawing Sheet

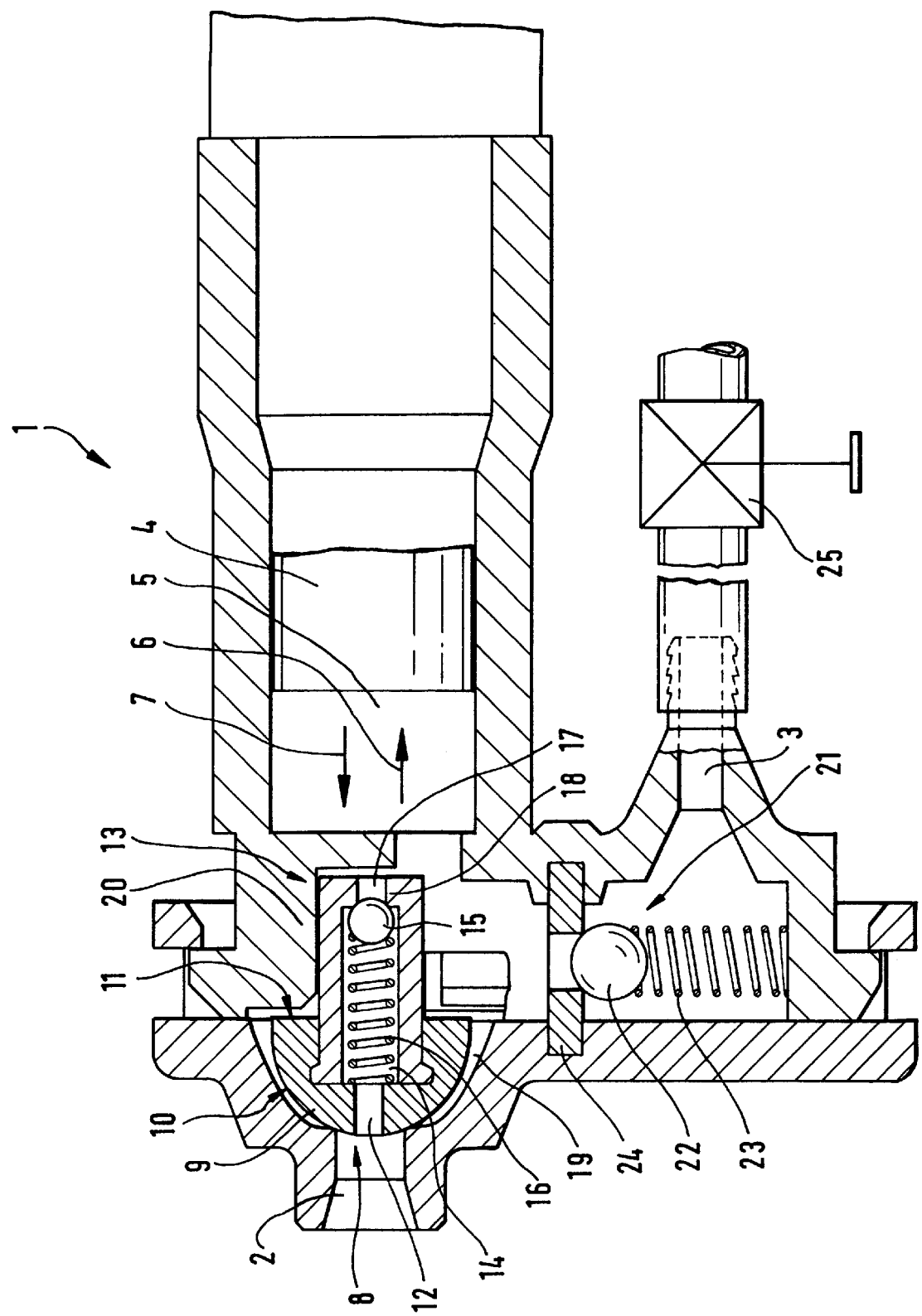

5,993,402

1

PRESSURE RELIEF VALVE FOR AN ORAL IRRIGATOR

FIELD OF THE INVENTION

This invention relates to a device for the care and cleaning of teeth and gums, with a pump which is adapted to be driven by an electric motor and has an inlet connected in particular to a liquid reservoir and provided with an inlet valve, an outlet connected in particular to a jet nozzle and provided with an outlet valve, as well as a pump cylinder which is connected to the inlet and the outlet and has a piston reciprocating therein, whereby liquid can be drawn from the inlet into the pump cylinder following which the drawn liquid can be delivered from the pump cylinder to the outlet.

A device of this type is known from European Patent Application EP 85 795 A1. In the oral irrigator therein described, a pump driven by an electric motor is provided with an inlet and an outlet. The inlet is connected to a liquid reservoir fillable with water, and the pump outlet is connected to a jet nozzle through a piece of hose of some length. Further, the inlet is provided with an inlet valve, and the outlet with an outlet valve. Located in the pump between the inlet and the outlet is a pump cylinder in which a piston is arranged for reciprocation. In the activated condition of the oral irrigator, water is drawn from the liquid reservoir through the pump inlet, to be subsequently forced through the pump outlet to the jet nozzle. As this occurs, the outlet valve is closed during the suction stroke of the piston, and the water is drawn through the open inlet valve. Conversely, during the subsequent pressure stroke of the piston, the inlet valve is closed, and the water is forced through the open outlet valve to the jet nozzle. A user may direct the jet nozzle to the oral cavity, using the exiting water jet for the care and cleaning of teeth and gums.

The electric on-off switch for the pump is accommodated in the jet nozzle. For this purpose, two electric wires are routed from the on-off switch in the interior of the long hose to the electric motor driving the pump. This enables the user to start and stop the water jet by turning the pump on and off by means of the electric on-off switch in the jet nozzle, and vice versa.

SUMMARY OF THE INVENTION

It is an object of the present invention to further develop the device of the type initially referred to in particular with a view to simplifying its design and manufacture.

According to the present invention, this object is accomplished in that the inlet valve includes a pressure relief valve through which liquid can be delivered from the pump cylinder to the inlet in the event of excess pressure building up.

By means of the present invention, it is possible to start the water jet and stop it again merely by shutting off the water supply to the jet nozzle, without the need to turn the pump on and off. With the water jet "turned on", the water is forced by the pump to the jet nozzle as before. By contrast, in shut-off condition, that is, with the water jet "turned off", the water, rather than being pumped to the jet nozzle, is returned to the inlet through the pressure relief valve. As this occurs, the pump continues running. Neither the pump nor the electric motor are exposed to overload because no excess pressure builds up in the pump, the water being instead returned to the inlet through the pressure relief valve.

Accordingly, this obviates the need for turning the electric motor driving the pump on and of f by means of an electric on-off switch on the jet nozzle when it is desired to start or stop the water jet. Instead, the delivery of the water jet is simply established or disconnected while the pump is running. The provision of an electric on-off switch directly on the jet nozzle is thus no longer necessary. It suffices to make provisions for shutting off the water at the jet nozzle.

Still further, the pressure relief valve also serves as a safeguard against pump overload in the event of a clogged condition of the jet nozzle or the hose leading to the jet nozzle.

This represents a simplified design of the oral irrigating apparatus and has attendant cost advantages. Electric wires or the like need no longer be routed to the jet nozzle, nor is it necessary to make provisions for protecting the electric on-off switch in the jet nozzle from the ingress of water. This simplified design of the oral irrigator of the present invention also affords manufacturing advantages. In particular, the manufacture of the long hose leading to the jet nozzle is materially simplified and also more economical because of the elimination of the electric wires.

It is another advantage of the present invention that with the water jet shut off, the water continuing to be delivered by the pump is directed through the pressure relief valve to the inlet and thence back to the liquid reservoir. The water is thus pumped back directly to the liquid reservoir. Any further valves or bypass hose or the like are not necessary. By allocating the pressure relief valve to the inlet valve, simplicity and economy of design and corresponding manufacture of the oral irrigator of the present invention are accomplished.

In an advantageous configuration of the present invention, provision is made for a closure member for opening and closing the inlet valve, said closure member having a through opening which is connected to the pressure relief valve. Resting against the inlet, the closure member is able to close the inlet during the pressure stroke of the piston. With the pressure relief valve closed, no water flows through the through opening. Only with the pressure relief valve open is it possible, during the pressure stroke of the piston, for water to be delivered from the pump cylinder through the pressure relief valve and the through opening to the inlet and onward to the liquid reservoir. The advantage of the configuration described is that it is straightforward in construction and that the object to enable water flow from the pump cylinder through the pressure relief valve to the inlet in the event of excess pressure is accomplished by such simple means.

In a further configuration of the present invention, the closure member is of hemispherical shape and the pump is provided with a hemispherically shaped inner chamber in which the closure member is received. The hemispherical shapes of the closure member and the inner chamber have the advantage of obviating the need for a spring or the like to urge the closure member against the inlet for closing. Instead, the hemispherical shape enables the closure member to move back and forth with ease under the action of the suction and pressure strokes. In consequence, the suction stroke of the piston causes the closure member to be lifted clear of the inlet, whereby the inlet valve is opened. In this arrangement, a low suction pressure will be sufficient as it is produced, for example, in the aspiration of air when water has not as yet reached the pump. During the pressure stroke of the piston, by contrast, the closure member is urged into engagement with the inlet, closing the inlet valve. The configuration described thus re quires fewer components, resulting in a low-cost construction of the oral irrigator of the present invention.

In an advantageous further development of the present invention, the pressure relief valve is mounted on the closure member and thereby connected directly with the through opening of the closure member. The closure member of the inlet valve and the pressure relief valve thus combine to form a unit. This has the advantage that the pressure relief valve necessitates nearly no additional space in the interior of the pump. It may even be convenient for the pressure relief valve to be integrally formed with the closure member of the inlet valve, at least in part. It is a further advantage of this design that the through opening of the closure member is directly connected to the pressure relief valve. Special hose couplings or the like are not necessary. Hence, this further development contributes, too, to achieving an overall simple and low-cost design and a correspondingly advantageous manufacture of the oral irrigator of the present invention.

Particularly suitably, the pressure relief valve includes a ball urged against an orifice by a spring and displaceable in opposition to the force of said spring in the event of excess pressure building up. This represents a simple but yet well-proven and low-cost configuration of a pressure relief valve which, in addition, is particularly well suited for combination with the closure member and for integration therein at least in part.

With this configuration of the pressure relief valve, the force of the spring can be used for adjustment of the value of the excess pressure at which the pressure relief valve opens. This enables in a particularly straightforward manner an adjustment of the pressure relief valve so that it does not open while the pump is running and the water jet is not shut off, thus preventing water from being pumped back to the liquid reservoir, whereas with the water jet shut off the pressure relief valve opens, enabling the water to return to the liquid reservoir. This adjustment can be accomplished by suitably selecting the spring of the pressure relief valve.

In an advantageous further development of the present invention, a shutoff valve is provided downstream of the outlet, in particular in the jet nozzle. The shutoff valve enables the user to set the water jet in motion, "turning it on", and to stop it again subsequently, "turning it off". This is accomplished only by shutting off the water supply to the jet nozzle while the pump continues running. The shutoff valve may be of a simple design allowing economy of manufacture.

Still further, it is advantageous to provide, separately from the jet nozzle, an electric on-off switch for the pump. Particularly suitably, the on-off switch for the pump is located on the housing of the oral irrigator. This has the advantage that the electric wires for the electric on-off switch are required to be routed over a short distance only, in particular not through the long hose to the jet nozzle. As will be apparent, this also represents a simplified design of the oral irrigator of the present invention.

BRIEF DESCRIPTION OF THE DRAWING

Further features, advantages and application possibilities of the present invention will become apparent from the subsequent description of embodiments illustrated in more detail in the accompanying drawing. It will be understood that any single feature and any combination of single features described and/or represented by illustration form the subject-matter of the present invention, irrespective of their summary in the claims and their back-reference.

The sole FIGURE of the drawing is a schematic sectional view of an embodiment of a pump of the present invention for a device for the care and the cleaning of teeth and gums.

DETAILED DESCRIPTION OF THE PREFERRED EMBODIMENT

In the FIGURE, a pump 1 for an oral irrigator is shown. The oral irrigator includes a liquid reservoir fillable with water by a user. The liquid reservoir is connected as through a hose to an inlet 2 of the pump 1. An outlet 3 of the pump 1 is connected to a jet nozzle by means of a further hose of preferably longer length. In the activated condition of the oral irrigator, the pump 1 draws the water from the liquid reservoir through the inlet 2, forcing it through the outlet 3 to the jet nozzle. The water jet produced by the jet nozzle can be used for the care and cleaning of the user's teeth and gums.

The pump 1 includes an electric motor with a drive shaft coupled through an eccentric gear arrangement and a connecting rod to a cylindrical piston 4 received in a pump cylinder 5. In the activated condition of the oral irrigator, the rotary motion of the drive shaft of the electric motor is converted by means of the eccentric gear arrangement and the connecting rod into a reciprocating motion of the piston 4. This motion is indicated in the Figure by the arrows 6 and 7, the motion of the piston 4 being composed of the suction stroke 6 and the pressure stroke 7.

The pump cylinder 5 is connected to the inlet 2 through an inlet valve 8. The inlet valve 8 has a closure member 9 which is of a hemispherical configuration, accordingly possessing a curved surface 10 and a plane surface 11. The closure member 9 contains a through opening 12 which extends from the curved surface to the plane surface 11 and is located normal to and on the center of the plane surface 11. The closure member 9 serves to open and close the inlet 2.

In the area of the plane surface 11, the closure member 9 is connected to a pressure relief valve 13. In particular, the pressure relief valve 13 is snappingly or threadably engaged with the closure member 9 of the inlet valve 8. The pressure relief valve 13 is cylindrically shaped and has a central through bore 14 disposed coaxially with the opening 12 of the closure member 9. The opening 12 of the closure member 9 thus merges directly into the bore 14 of the pressure relief valve 13.

Received in the bore 14 of the pressure relief valve 13 are a ball 15 and a spring 16. The spring 16 is arranged such as to urge the ball 15 against an inwardly extending projection 18 forming an orifice 17 at the free end of the pressure relief valve 13. In this position shown in the FIGURE, the ball 15 engages the orifice 17, the pressure relief valve 13 being accordingly closed.

The pump 1 has a hemispherically shaped inner chamber 19, with a curvature somewhat greater than the curvature of the curved surface 10 of the closure member 9. Accommodated in the inner chamber 19 is the closure member 9 with its curved surface 10.

Still further, the pump 1 has walls 20 or projections or the like which serve to guide the closure member with the pressure relief valve 13 mounted thereon in such manner as to enable a reciprocating motion in the direction of the through opening 12 of the closure member 9. In the position illustrated in the FIGURE, the curved surface 10 of the closure member 9 is in engagement with the inlet 2, so that communication is established only between the inlet 2 and the opening 12 of the closure member 9 and the bore 14 of the closed pressure relief valve 13, but not with the inner chamber 19 or the pump cylinder 5. In the position not illustrated in the FIGURE, the closure member 9 is disengaged from the inlet 2, a connection being established from the inlet 2 past the closure member 9 to the pump cylinder 5 of the pump 1.

The pump cylinder 5 is further connected through an outlet valve 21 to the outlet 3. The outlet valve 21 has a ball 22 urged by a spring 23 against an apertured disk 24, closing the disk. In this position which is illustrated in the FIGURE, the outlet valve 21 is closed.

With the oral irrigator activated, the suction stroke of the piston 4 in the direction of arrow 6 causes the inlet valve 8 to open. This is accomplished in that the suction stroke 6 of the piston 4 causes a displacement, in the same direction as the piston 4, of the closure member 9 of the inlet valve 8 together with the pressure relief valve 13 by reason of the suction pressure generated and the resulting flow in the interior of the pump 1. Water is thus allowed to flow from the inlet 2 past the closure member 9 into the inner chamber 19 and onward into the pump cylinder 5. During this suction stroke 6 of the piston 4, the pressure relief valve 13 is closed because the ball 15 is urged against the orifice 17 on account of the force of the spring 16, closing the orifice. During the suction stroke 6 of the piston 4, the outlet valve 21 is likewise closed because the force of the spring 23 acts to urge the ball 22 against the apertured disk 24, closing it.

In consequence, during the suction stroke 6 of the piston 4, water is drawn from the inlet 2 through the inlet valve 8 into the pump cylinder 5, so that on termination of the suction stroke 6 of the piston 4, the pump cylinder 5 is filled with water.

The subsequent pressure stroke of the piston in the direction of arrow 7 causes the outlet valve 21 to open. In this process, therefore, the pump pressure generated by the piston 4 causes a slight displacement of the ball 22 in opposition to the force of the spring 23, disengaging the ball 22 from the apertured disk 24 so that it is no longer closed. As a result, the water held in the pump cylinder 5 is pumped through the outlet valve 21 to the outlet 3.

At the beginning of this pressure stroke of the piston 4 in the direction of arrow 7, the inlet valve 8 is closed because the closure member 9 is displaced in the same direction as the piston 4 by the movement of the piston 4 and the pump pressure thereby generated and the resulting flow in the interior of the pump 1. Hence, the closure member 9 is in engagement with the inlet 2 and closes it, so that water is prevented from flowing past the closure member 9 to the inlet 2.

In addition, the pressure relief valve 13 remains also closed during the pressure stroke 7 of the piston 4. This is accomplished by selecting the force of the spring 16 sufficiently high to prevent the ball 15 from being displaced against the spring 16 by the pressure occurring during the pressure stroke 7.

Overall, therefore, during the pressure stroke 7 of the piston 4, water is delivered only to the outlet 3 and not back to the inlet 2. At the end of the pressure stroke of the piston 4, there is essentially no water left in the pump cylinder 5.

Provided in the interior of the jet nozzle is a shutoff valve 25 which is connected through the long hose with the outlet 3 of the pump 1. The shutoff valve 25 is suited for interruption and passage of the afflux of water to the jet nozzle produced by the pump 1. In the simplest case, the shutoff valve 25 may involve a clamping device or the like by means of which the hose carrying the water is compressed such as to inhibit the passage of water and its discharge from the jet nozzle.

In the foregoing description of the mode of operation of the oral irrigator according to the FIGURE, it has been assumed that the shutoff valve 25 is open.

However, when the shutoff valve 25 is closed in the activated condition of the pump 1, water is prevented from exiting the jet nozzle. During the pressure stroke 7 of the piston 4, water is then prevented from being pumped out of the pump cylinder 5 through the outlet 3 to the jet nozzle. This has the effect that during the pressure stroke 7 the pressure in the interior of the pump 1 and in particular in the pump cylinder 5 increases. When this pump pressure exceeds a specified value, the pressure relief valve 13 opens. The pump pressure thus acts to displace the ball 15 in opposition to the force of the spring 16, and water is allowed to flow through the orifice 17 formed by the projection 18 to the inlet 2. Accordingly, the increased pressure in the pump cylinder 5 is reduced through the orifice 17. The pressure relief valve 13 remains open until the pressure in the interior of the pump 1 has dropped to the specified value. This value corresponds to the force of the spring 16 and is thus adjustable by appropriately selecting the spring 16.

By means of the shutoff valve 25, therefore, the water in the jet nozzle is shut off while the pump 1 continues running. The water delivered by the continued running of the pump 1 is fed through the pressure relief valve 13 to the inlet 2 and thus back to the liquid reservoir. overloading of the electric motor driving the pump 1 or an excessive pressure in the interior of the pump 1 are avoided by the pressure relief valve 13.

The electric on-off switch for the electric motor of the pump 1 is provided separately from the jet nozzle, being located in particular on the housing of the oral irrigator in which the pump 1 is received.

We claim:

1. An oral irrigation device for cleaning an oral cavity of a user, comprising
    a reservoir for containing a supply of fluid,
    a pump having a pump body forming a chamber defined by rigid immovable wall portions, the chamber having an outlet and a single inlet and said chamber being disposed in fluid communicating relation therebetween, the inlet being coupled to the reservoir for receiving fluid and the pump pressurizing increased flow of the fluid from the reservoir through the outlet,
    an electric motor coupled to the pump,
    a handpiece for receiving the fluid from the pump and adapted to deliver the fluid to the oral cavity of the user,
    a single hose coupling the outlet to the handpiece,
    a throttle valve disposed on the handpiece and selectively operable by the user during use to throttle fluid delivery therethrough, the throttle valve being moveable between a first position and a second position, the first position permitting a greater fluid delivery flow than the second position, said throttle valve not being electrically coupled to the motor,
    an outlet check valve responsive to pump pressure to permit forward flow from the outlet to the handpiece, said outlet check valve being biased to prevent reverse flow from the handpiece to the inlet,
    a single inlet check valve responsive to pump suction to enable fluid flow from the reservoir independently of the handpiece throttle valve position, the outlet check valve being closed in response to the pump suction,
    a single relief check valve biased closed to prevent reverse flow back to said reservoir, the relief check valve opening responsive to pump pressure coincident with the throttle valve being at the second position reducing fluid delivery, to enable fluid flow from the chamber to the reservoir, wherein one of said inlet and outlet check valves is urged closed whenever the other is open during operation of the pump, and wherein said inlet check valve and said relief check valve are disposed adjacent said single inlet and collectively occupy an area of said inlet receiving, fluid, whereby during pump suction the handpiece is fluidicly decoupled by the outlet check valve from the inlet check valve and the chamber, the inlet check valve being opened while the outlet check valve being closed in response to pump suction, and in response to pump pressure only when the handpiece throttle valve is in the second position the chamber is fluidicly coupled for reverse flow back to the reservoir by opening the relief check valve to reduce an undesired overpressure.

2. The irrigation device of claim 1, wherein the relief check valve is in fluid communication at its inlet side with an outlet side of the inlet check valve and is in fluid communication at its outlet side with an inlet side of the inlet check valve.

3. The irrigation device of claim 2, wherein the inlet check valve has a cylindrical bore within which the relief check valve is disposed, the cylindrical bore defining a through opening in communication with the inlet.

4. The irrigation device of claim 1, 2 or 3, wherein the inlet check valve is not urged by spring bias into closing the inlet, whereby a force of pump pressure closes the inlet check valve.

5. The irrigation device of claim 1, wherein the outlet check valve is disposed within the pump housing before the outlet, thereby bounding on an upstream side thereof a fluid receiving portion of the chamber that receives fluid during pump suction.

6. The irrigation device of claim 1, wherein the pump body comprises two major fixed wall sections, a first said fixed wall section defining a piston cylinder and the outlet, a second said fixed wall section defining the inlet and having a recess therein in which the inlet check valve is at least partially disposed, said first and second wall sections being fixedly connected to one another and defining therebetween a cavity in which is located said pump chamber.

7. The irrigation device of claim 6, wherein the outlet check valve is disposed in the cavity between said first and second wall sections.

8. The irrigation device of claim 7, wherein the outlet check valve is supported on confronting surfaces disposed on each of said first and second wall sections.

9. The irrigation device of claim 1, wherein the pump comprises a piston pump having a piston supported for reciprocation within a piston cylinder in fluid communication with the pump chamber, the inlet check valve comprises an at least partially displaceable closure member, and the pump cylinder being arranged substantially parallel to a displacement direction of the closure member, whereby during pump suction and pressure strokes a force of the moving piston displaces the closure member in generally the same direction as the piston motion.

10. The irrigation device of claim 9, wherein the inlet check valve is oriented downward in the closed position, whereby a force of gravity assists displacing the closure member to close the inlet during the pump pressure stroke.

11. The irrigation device of claim 9, wherein the inlet check valve has a cylindrical bore within which the relief check valve is disposed, the cylindrical bore defining a through opening in communication with the inlet, whereby during pump suction and pressure strokes a force of the moving piston displaces the closure member together with the relief check valve in about the same direction as the piston.

12. The irrigation device of claim 9 or 11, wherein the inlet check valve is non-biasedly supported at the inlet, whereby a force of suction and pressure, alternately, opens and closes the inlet check valve.

13. The irrigation device of claim 9, wherein the chamber has a receiving portion that receives fluid during pump suction, a major portion of the receiving portion being disposed substantially within a region defined by a projection of an area of the piston in the direction of the piston stroke, the inlet check valve and relief check valve each being located within the major portion of the chamber receiving portion, whereby fluid during the suction cycle is moved in the major portion region generally with the piston stroke.

14. The irrigation device of claim 13, wherein the handpiece throttle valve second position is a shut-off position in which the handpiece is disabled from fluid delivery, whereby the relief check valve remains closed when the handpiece throttle valve is in a position other than the fluid delivery-disabling second position.

15. The irrigation device of claim 1, wherein the inlet check valve and the relief valve are disposed in the chamber, the chamber being common to the pump suction side and the pump pressure side.

16. The irrigation device of claim 1, wherein the handpiece throttle valve second position is a shut-off position in which the handpiece is disabled from fluid delivery, whereby the relief check valve remains closed when the handpiece throttle valve is in a position other than the fluid delivery-disabling second position.

17. The irrigation device of claim 16, wherein the throttle valve is a two-position on/off switch displaceable to either the first position corresponding to fluid delivery from the handpiece and the second position corresponding to the shut-off position.

18. The irrigation device of claim 16, wherein the throttle valve when activated to the shut-off position by the user remains in the shut-off position until the throttle valve is reactivated by the user.

19. The irrigation device of claim 1, wherein the pump chamber has a concavity in a wall portion, the inlet check valve being seated in the concavity.

20. The irrigation device of claim 19, wherein the inlet check valve has a closure member disposed within the concavity when the inlet check valve is in a sealed position during a pump pressure cycle, the closure member displacing a small amount and remaining substantially within the concavity during a pump suction cycle.

21. The irrigation device of claim 19, wherein the inlet check valve has a closure member having a substantially hemispherical outer shape, the chamber concavity having a shape corresponding thereto.

22. The irrigation device of claim 1 further comprising an electrical on-off switch disposed on a base housing and controlling the pump motor.

* * * * *